US010765347B2

(12) United States Patent
Fuke et al.

(10) Patent No.: US 10,765,347 B2
(45) Date of Patent: Sep. 8, 2020

(54) GAIT ANALYSIS DEVICE AND COMPUTER PROGRAM PRODUCT

(71) Applicant: KABUSHIKI KAISHA TOSHIBA, Tokyo (JP)

(72) Inventors: Sawa Fuke, Kanagawa (JP); Takuji Suzuki, Kanagawa (JP); Kenta Cho, Kanagawa (JP)

(73) Assignee: TDK Corporation, Tokyo (JP)

( * ) Notice: Subject to any disclaimer, the term of this patent is extended or adjusted under 35 U.S.C. 154(b) by 214 days.

(21) Appl. No.: 13/665,081

(22) Filed: Oct. 31, 2012

(65) Prior Publication Data
US 2013/0110010 A1 May 2, 2013

(30) Foreign Application Priority Data
Oct. 31, 2011 (JP) .................................. 2011-238246

(51) Int. Cl.
A61B 5/11 (2006.01)
A61B 5/00 (2006.01)

(52) U.S. Cl.
CPC ............ *A61B 5/112* (2013.01); *A61B 5/1117* (2013.01); *A61B 5/6823* (2013.01); *A61B 2562/0219* (2013.01)

(58) Field of Classification Search
CPC ......... A61B 5/111; A61B 5/114; A61B 5/112; A61B 5/1117; A61B 5/1123
USPC ........................................................ 600/595
See application file for complete search history.

(56) References Cited

U.S. PATENT DOCUMENTS

| 7,612,681 | B2 * | 11/2009 | Azzaro | ................. | A61S 5/1113 340/573.1 |
| 2002/0116080 | A1 * | 8/2002 | Birnbach | ............. | A61B 5/0002 700/66 |
| 2006/0195050 | A1 * | 8/2006 | Alwan | ................. | A61B 5/1038 600/595 |

(Continued)

FOREIGN PATENT DOCUMENTS

| CN | 101327125 | 12/2018 |
| EP | 2 005 887 | 12/2008 |

(Continued)

OTHER PUBLICATIONS

Office Action dated Apr. 1, 2014 in counterpart Chinese Patent No. 201210425490.0 and English-language translation thereof.
(Continued)

*Primary Examiner* — Daniel L Cerioni
*Assistant Examiner* — Yasmeen S Warsi
(74) *Attorney, Agent, or Firm* — Nixon & Vanderhye, P.C.

(57) ABSTRACT

According to an embodiment, a gait analysis device includes a measuring unit configured to measure a subject's motion; a determining unit configured to determine a walking start point in time at which the subject starts walking based on the subject's motion; a feature quantity calculator configured to, when the walking start point in time is determined, calculate a feature quantity of the subject's motion measured during a predetermined time period starting from the walking start point in time as a time period in which the subject's motion is not stabilized; and an estimating unit configured to estimate a subject's walking condition based on the feature quantity.

7 Claims, 7 Drawing Sheets

(56) References Cited

U.S. PATENT DOCUMENTS

| | | | | |
|---|---|---|---|---|
| 2006/0284979 A1* | 12/2006 | Clarkson | ................ | A61B 5/061 |
| | | | | 348/143 |
| 2009/0240461 A1* | 9/2009 | Makino | ................ | G01C 22/006 |
| | | | | 702/141 |
| 2010/0070235 A1* | 3/2010 | Cho et al. | ..................... | 702/141 |
| 2010/0185570 A1* | 7/2010 | Ou | .......................... | G06F 3/017 |
| | | | | 706/12 |
| 2011/0246122 A1 | 10/2011 | Iketani et al. | | |
| 2012/0016624 A1 | 1/2012 | Caritu et al. | | |

FOREIGN PATENT DOCUMENTS

| | | | | |
|---|---|---|---|---|
| JP | 2006-175206 | | 7/2006 | |
| JP | 2011-92696 | | 5/2011 | |
| JP | 2011163861 A | * | 8/2011 | |
| JP | 2011-215951 | | 10/2011 | |
| JP | 4911259 | | 12/2011 | |
| WO | 2010/076313 | | 7/2010 | |
| WO | WO 2011002788 A2 | * | 1/2011 | ........... A61B 5/1038 |

OTHER PUBLICATIONS

Office Action dated Aug. 26, 2014 in counterpart Japanese Patent No. 2011-238246 and English-language translation thereof.
Office Action dated Sep. 10, 2014 in counterpart Chinese Patent No. 201210425490.0 and English-language translation thereof.
Notification of Reasons for Refusal dated Apr. 26, 2016 in counterpart JP Application No. 2015-088627 and English-language machine translation of same (Data Source: EPO Global Dossier; Translated May 30, 2016; Dictionary Last Updated: Apr. 21, 2016).

* cited by examiner

| LABEL | HIGH-RISK | CAREFUL | SAFE |
|---|---|---|---|
| SCORE | 45 OR LESS | 46 TO 50 | 51 OR MORE |

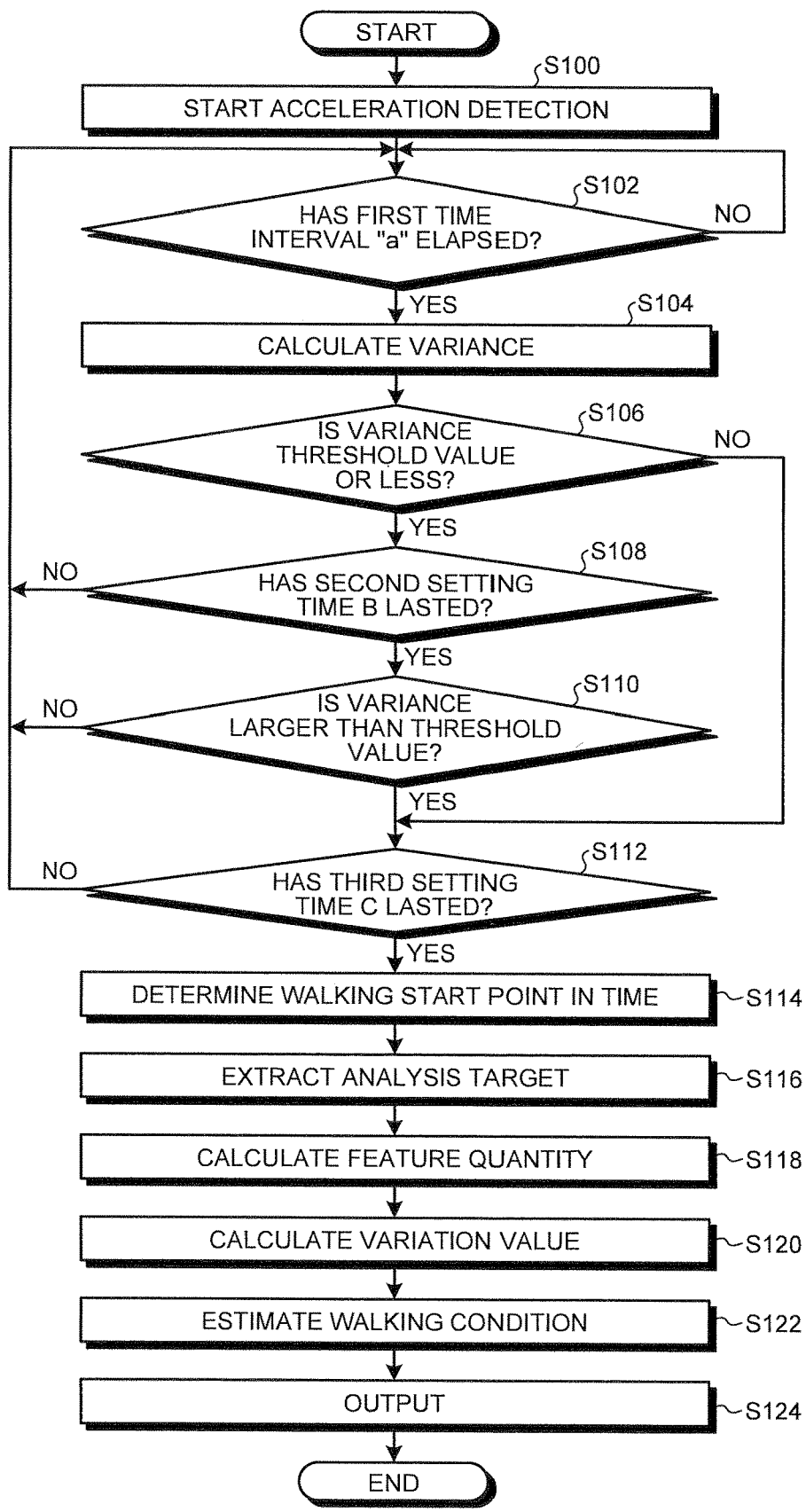

GAIT ANALYSIS DEVICE AND COMPUTER PROGRAM PRODUCT

CROSS-REFERENCE TO RELATED APPLICATIONS

This application is based upon and claims the benefit of priority from Japanese Patent Application No. 2011-238246, filed on Oct. 31, 2011; the entire contents of which are incorporated herein by reference.

FIELD

An embodiment described herein relates generally to a gait analysis device and a computer program product.

BACKGROUND

Devices that evaluate gait motion using various kinds of sensor devices have been developed for the purpose of observing the course of a disease, preventing falls, and the like. In medical practice, a subject is required to do an action (standing on one foot or the like) needing balance ability, and the subject's behavior is observed to determine a fall risk.

However, in the related art, measurement and estimation of a disease degree are performed under the assumption that the subject keeps walking, and so it is difficult to estimate a walking condition and a fall risk in a short time from a start of walking. In addition, the technique executed in the medical practice has a problem in that the subject has a risk and feels pressured since the subject is required to do an action needing balance ability.

BRIEF DESCRIPTION OF THE DRAWINGS

FIG. 8 is a flowchart illustrating an operation of a gait analysis device according to an embodiment.

DETAILED DESCRIPTION

According to an embodiment, a gait analysis device includes a measuring unit configured to measure a subject's motion; a determining unit configured to determine a walking start point in time at which the subject starts walking based on the subject's motion; a feature quantity calculator configured to, when the walking start point in time is determined, calculate a feature quantity of the subject's motion measured during a predetermined time period starting from the walking start point in time as a time period in which the subject's motion is not stabilized; and an estimating unit configured to estimate a subject's walking condition based on the feature quantity.

Figure 1:
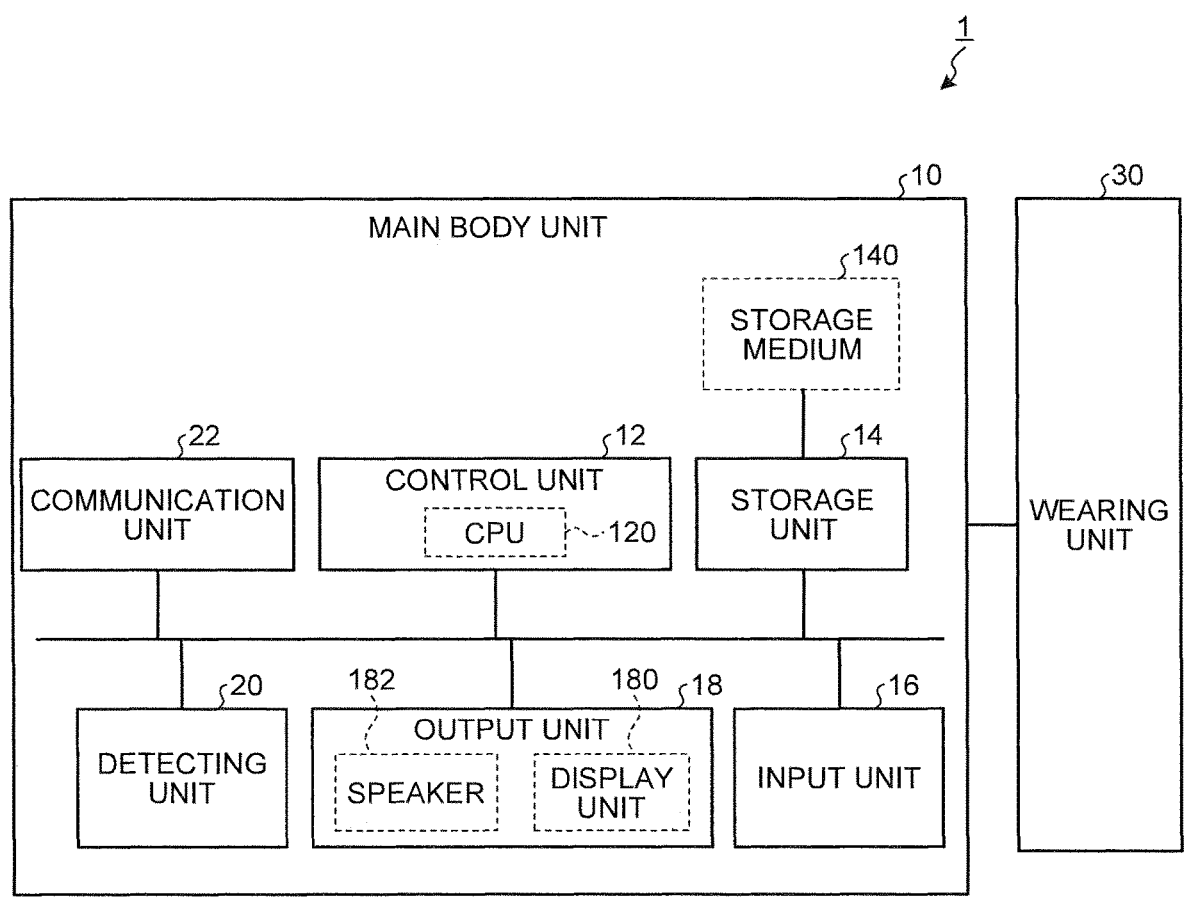
FIG. 1 is a hardware configuration diagram of a gait analysis device according to an embodiment.

An embodiment will be described in detail with reference to the accompanying drawings. FIG. 1 is a diagram illustrating a configuration of a gait analysis device 1 according to the embodiment. As illustrated in FIG. 1, the gait analysis device 1 includes a main body unit 10 and a wearing unit 30.

The main body unit 10 includes a control unit 12, a storage unit 14, an input unit 16, an output unit 18, a detecting unit 20, and a communication unit 22. The control unit 12 includes, for example, a central processing unit (CPU) 120, and controls respective components constituting the main body unit 10. The storage unit 14 includes a read only memory (ROM), a random access memory (RAM), and the like, which are not illustrated in the drawing, and stores therein a program executed by the control unit 12, data used for the control unit 12 to execute a program, and the like. Further, a storage medium 140 such as a memory card having a function of transmitting/receiving a program and data to/from the storage unit 14 is detachably attached to the main body unit 10.

The input unit 16 includes, for example, an input key or a switch, and receives a user's input to the main body unit 10. The output unit 18 includes, for example, a display unit 180 such as a liquid crystal panel, a speaker 182 that outputs a sound or the like, and a vibrator (not illustrated). The output unit 18 outputs a state of the main body unit 10 and a processing operation result of the main body unit 10 through at least one of a screen display, a sound, and vibration. The input unit 16 may be integrated with the display unit 180 through a touch panel.

The detecting unit 20 includes, for example, a tri-axial acceleration sensor having a sampling frequency of 128 Hz, and has an acceleration measurement range of, for example, ±6 G or more. For example, when the gait analysis device 1 is worn on a gait analysis subject, the detecting unit 20 detects acceleration in a vertical direction, acceleration in a moving direction of the subject, and acceleration in a horizontal direction (a left-right direction) almost orthogonal to the moving direction of the subject (acceleration in three directions).

The communication unit 22 includes a general-purpose interface that performs communication with the outside, and is configured to be connectable to, for example, any one of wired communication, long-distance wireless communication, and near field communication (NFC).

For example, the wearing unit 30 is configured with a belt or the like wound on the subject's waist, and for example, the main body unit 10 is worn near the subject's waist.

Figure 2:
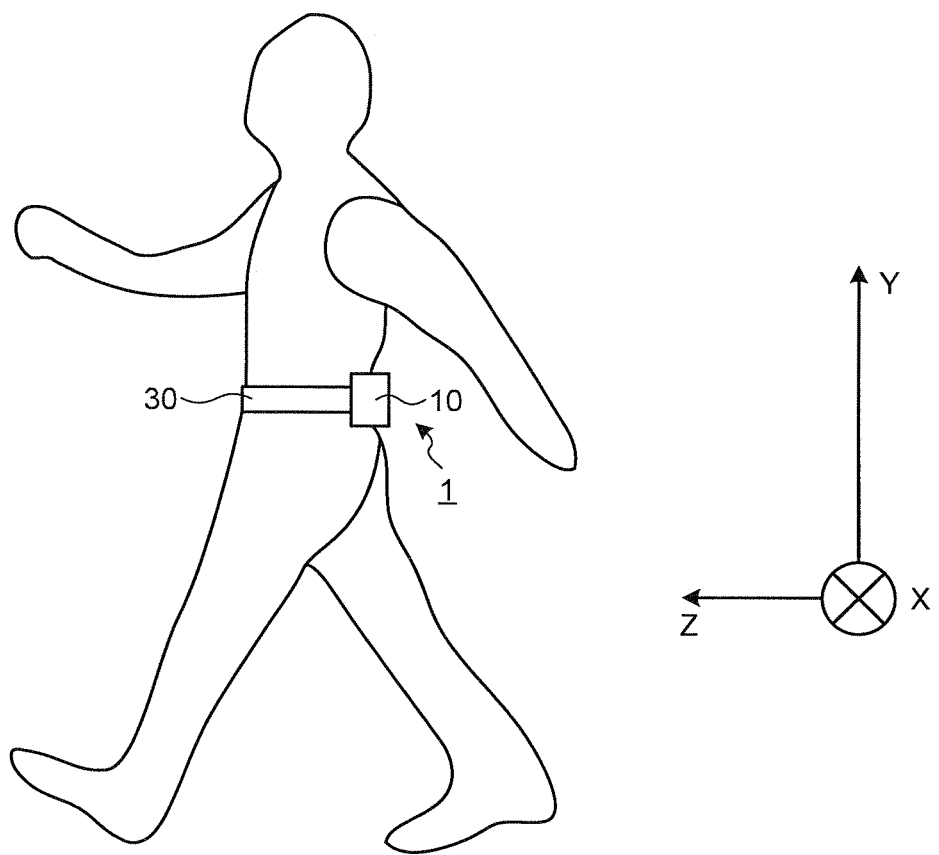
FIG. 2 is a schematic diagram illustrating a mounting state of a gait analysis device according to an embodiment.

FIG. 2 is a schematic diagram illustrating a state in which the gait analysis device 1 is worn near the subject's waist and directions of acceleration measured by the gait analysis device 1. As illustrated in FIG. 2, when worn near the subject's waist, the gait analysis device 1 detects acceleration in the vertical direction (a Y direction), acceleration in the moving direction of the subject (a Z direction), and acceleration in the horizontal direction (an X direction) almost orthogonal to the moving direction of the subject.

Figure 3:
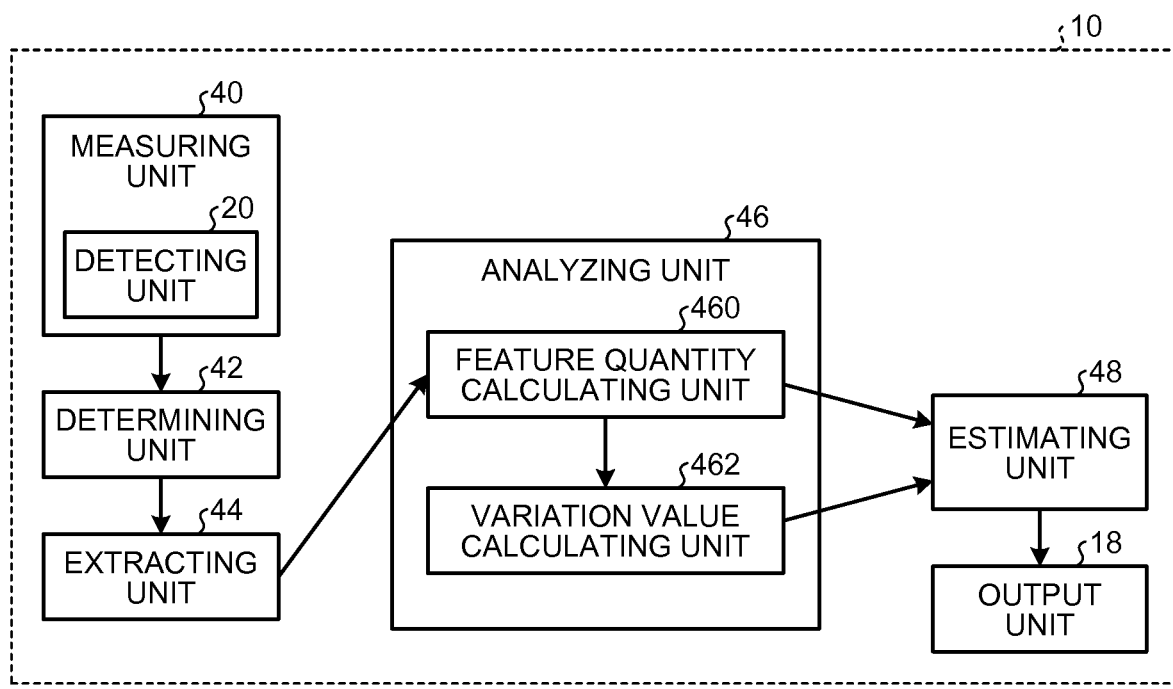
FIG. 3 is a functional block diagram illustrating a gait analysis device according to an embodiment.
Figure 4:
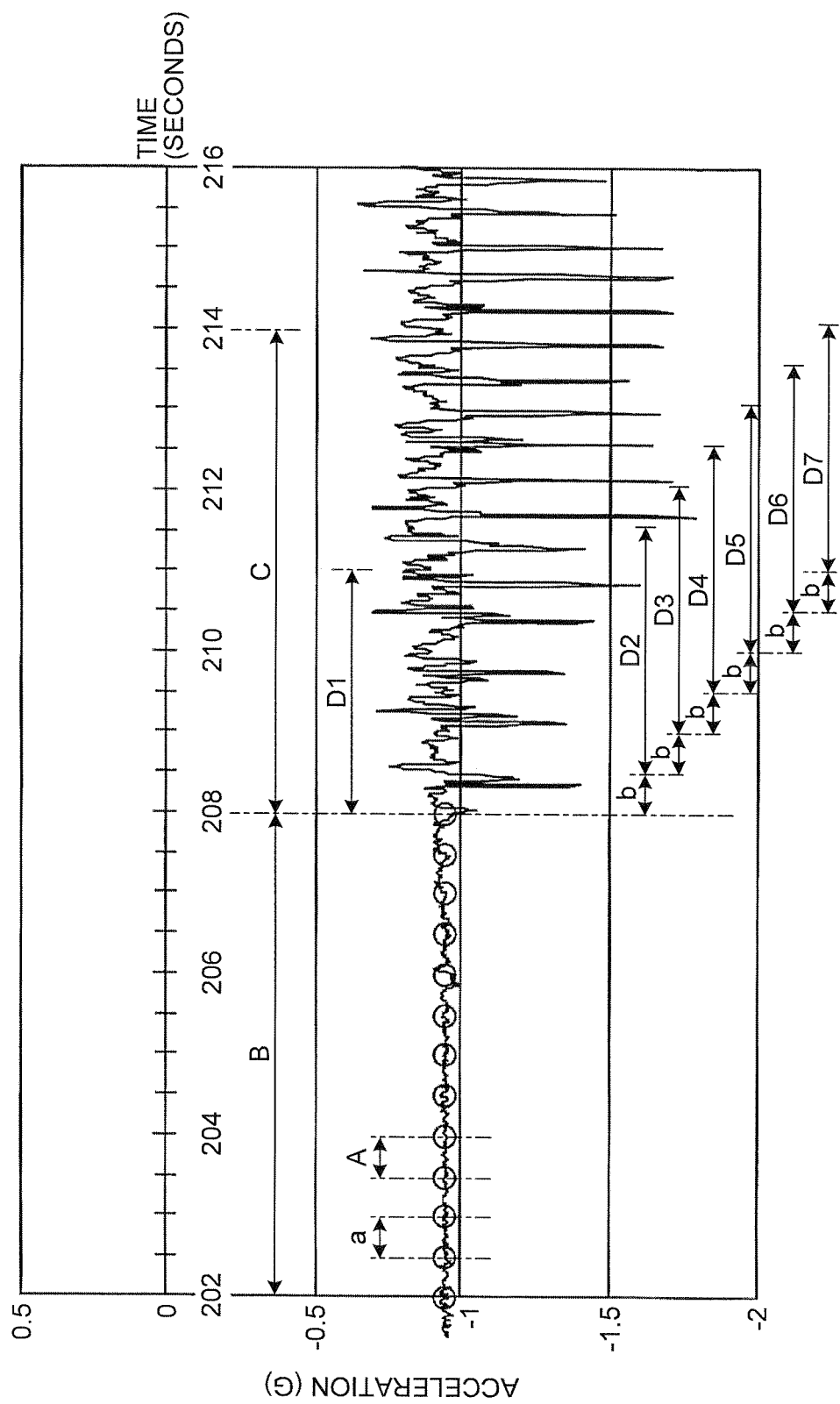
FIG. 4 is a graph illustrating a relation among acceleration, a determination result, and an analysis target.

Next, a function of the gait analysis device 1 will be described. FIG. 3 is a block diagram illustrating an outline of a function of the gait analysis device 1. FIG. 4 is a graph illustrating acceleration data detected by the detecting unit 20, a determination result of a determining unit 42 which will be described later, and an analysis target extracted by an extracting unit 44.

As illustrated in FIG. 3, the gait analysis device 1 includes a measuring unit 40, the determining unit 42, the extracting unit 44, an analyzing unit 46, an estimating unit 48, and the output unit 18. The output unit 18 illustrated in FIG. 3 corresponds to the output unit 18 illustrated in FIG. 1.

The measuring unit 40 detects the subject's motion. Specifically, the measuring unit 40 includes the detecting unit 20, and detects, for example, acceleration in three directions which changes according the subject's motion and measures the subject's motion (acceleration). For example, when power of the main body unit 10 is turned on, the measuring unit 40 continuously measures acceleration in three directions which is used to output a result of estimating the subject's walking condition through the gait analysis device 1. For example, all acceleration data measured by the measuring unit 40 is stored in the storage unit 14 (FIG. 1) together with a time until no longer necessary.

The determining unit 42 determines whether or not the subject has started walking based on the measurement result of the measuring unit 40. Specifically, the determining unit 42 first acquires acceleration data stored in the storage unit 14, and calculates a variance of acceleration data measured by the measuring unit 40 at predetermined time intervals (at first time intervals a) within a predetermined time frame (a first setting time period A). For example, the determining unit 42 calculates a variance of acceleration data measured by the measuring unit 40 newly for 0.5 seconds (A=0.5 seconds) at intervals of 0.5 seconds (a=0.5 seconds) as illustrated in FIG. 4. Here, when the sampling frequency of the detecting unit 20 is 128 Hz, the measuring unit 40 measures 64 pieces of acceleration data per direction within the first setting time period A (A=0.5 seconds). The first time interval "a" is preferably 0.5 seconds or less. The first setting time period A may be set to be longer than the first time interval "a".

Next, when a time period in which the variance of the acceleration data is equal to or less than a predetermined threshold value (threshold value σ) lasts for a second setting time period B or more and then a time period in which the variance of the acceleration data is larger than the threshold value σ lasts for a third setting time period C or more, the determining unit 42 (FIG. 3) determines, as a walking start point in time at which the subject has started walking, a point in time at which the variance of the acceleration data exceeds the threshold value σ (or alternatively, a point in time at which it is lastly determined that the variance of the acceleration data is equal to or less than the threshold value σ). For example, the threshold value σ is set to 0.04. Preferably, each of the second setting time period B and the third setting time period C has a value having a range of 2 seconds to 6 seconds.

For example, as illustrated in FIG. 4, when a time period in which the variance of the acceleration data is equal to or less than threshold value σ lasts for 6 seconds (the second setting time period B=6 seconds) or more and then a time period in which the variance of the acceleration data is larger than the threshold value σ lasts for 6 seconds (the third setting time period C=6 seconds) or more, the determining unit 42 retroactively determines, as the walking start point in time at which the subject has started walking, a point in time at which the variance of the acceleration data exceeds the threshold value σ (a start timing of the third setting time period C). In the example illustrated in FIG. 4, at 214 seconds (timed by the measuring unit 40), the determining unit 42 determines that the subject has started walking at 208 seconds. In this way, the determining unit 42 determines the walking start point in time, and determines whether or not the subject has started walking. Here, the determining unit 42 may be configured to calculate a standard deviation instead of a variance.

Here, when the determining unit 42 determines that the subject has started walking, the extracting unit 44 (FIG. 3) extracts data set for analysis from the measurement result of the measuring unit 40. Specifically, when the determining unit 42 determines that the subject has started walking, the extracting unit 44 extracts the acceleration data measured by the measuring unit 40 from acceleration data stored in the storage unit 14 during an extraction time period, that is, until a fourth setting time period D elapses from the walking start point in time. For example, the fourth setting time period D (the extraction time period) is set to 3 seconds.

In addition, the extracting unit 44 also extracts a plurality of pieces of acceleration data measured by the measuring unit 40 from the acceleration data stored in the storage unit 14 during a plurality of other extraction time periods obtained by sequentially delaying a start timing of the extraction time period from the walking start point in time by a predetermined time interval (a second time interval b).

For example, as illustrated in FIG. 4, when the determining unit 42 determines that the subject has started walking, the extracting unit 44 extracts the acceleration data measured by the measuring unit 40 during a extraction time period D1, that is, until 3 seconds (the fourth setting time period D=3 seconds) elapse from the walking start point in time. Further, the extracting unit 44 extracts six sets of acceleration data measured by the measuring unit 40. For example, during six other extraction time periods D2 to D7 obtained by sequentially delaying the start timing of the extraction time period from the walking start point in time by an interval of 0.5 seconds (the second time interval b=0.5). In the following, when there is no need to distinguish among the extraction time periods D1 to D7, the extraction time periods D1 to D7 may be collectively referred to simply as an extraction time period D (or the fourth setting time period D). Then, the acceleration data extracted by the extracting unit 44 is corresponded to data set for analysis used in the analyzing unit 46.

Figure 5:
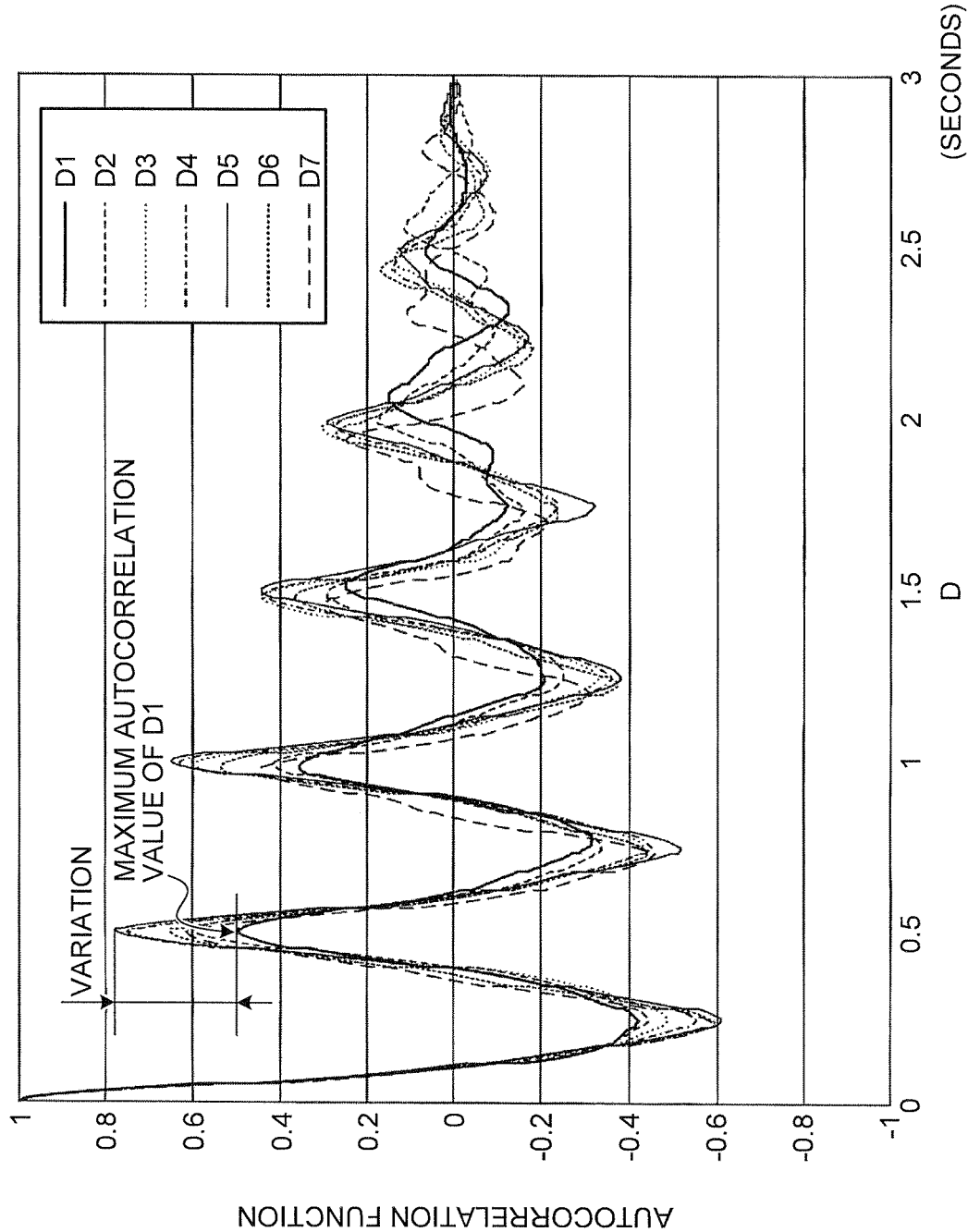
FIG. 5 is a graph illustrating an analysis example of a feature quantity calculation.

The analyzing unit 46 (FIG. 3) includes a feature quantity calculating unit 460 and a variation value calculating unit 462. The feature quantity calculating unit 460 calculates a feature quantity of acceleration data extracted by the extracting unit 44. Specifically, the feature quantity calculating unit 460 receives the data during the period of analysis extracted by the extracting unit 44, calculates, for example, an autocorrelation function of acceleration data in the vertical direction for each extraction time period D, for example, as illustrated in FIG. 5, and sets a first peak value (or a second peak value) as a maximum autocorrelation value. The feature quantity calculating unit 460 may be configured to filter the data sets to pass low frequency components in the data sets and then calculate the autocorrelation function. In FIG. 5, the extraction time period D is simply denoted by D, and the extraction time periods D1 to D7 are simply denoted by D1 to D7, respectively. The feature quantity calculating unit 460 outputs, as the feature quantity of each extraction time period D, each calculated maximum autocorrelation value to the variation value calculating unit 462 and the estimating unit 48.

The autocorrelation function calculated by the feature quantity calculating unit 460 has a value other than zero (0) when the acceleration data has periodicity, and has characteristics of which the value increases as the amplitude of acceleration data increases and noise decreases. For example, as illustrated in FIG. 5, the maximum autocorrelation value in the extraction time period D1 is smaller than each value in the extraction time periods D2 to D7. In other words, the extraction time period D1 is a transition state between a state (for example, a still state) in which the subject does not a dynamic motion and a state in which motion is stabilized. Therefore, in the extraction time period D1, the amplitude of acceleration data is considered to be small and the periodicity is considered to be low.

The feature quantity calculating unit 460 may be configured to calculate, as the feature quantity, left-right symmetry of the data sets for analysis extracted by the extracting unit 44 among the acceleration data in the left-right direction detected by the detecting unit 20. For example, the feature quantity calculating unit 460 may calculate, as the feature quantity, a mean value of the acceleration data in the left-right direction (the X direction) detected by the detecting unit 20 in each extraction time period D.

The variation value calculating unit 462 (FIG. 3) calculates a numerical value (a variation value) serving as an index of a variation in the maximum autocorrelation value of each the extraction time period D, which is calculated by the feature quantity calculating unit 460. For example, the variation value calculating unit 462 calculates a variance or a standard deviation of the maximum autocorrelation value (see a variation illustrated in FIG. 5) of each extraction time period D or a value using the sum of differences between the maximum autocorrelation value of the extraction time period D used as a reference and the maximum autocorrelation values of the other the extraction time periods D as the variation value. Here, when the subject's motion is stabilized, the variation in the maximum autocorrelation value is considered to decrease.

The variation value calculating unit 462 may be configured to calculate a variation value of the left-right symmetry of the analysis target extracted by the extracting unit 44 with respect to the acceleration in the left-right direction detected by the detecting unit 20. For example, the variation value calculating unit 462 may calculate, as the variation value, a variance of the mean values of the acceleration data in the left-right direction (the X direction), which is calculated by the feature quantity calculating unit 460 in each extraction time period D.

Here, since a subject having excellent balance ability early enter a state of steady gate, in case of a subject having excellent balance ability, a variation in the feature quantity of each extraction time period D is considered to promptly decrease.

The estimating unit 48 receives the feature quantity calculated by the feature quantity calculating unit 460 and the variation value calculated by the variation value calculating unit 462, and estimates the subject's walking condition using at least one of the received feature quantity and the variation value.

For example, the estimating unit 48 receives, as inputs, the maximum autocorrelation value of the extraction time period D1 and the variance of the maximum autocorrelation values of the extraction time periods D1 to D7, and classifies the subject's walking condition into three classes of "safe," "careful (cautious)," and "high-risk" using a classifier.

For example, the estimating unit 48 uses an algorithm of a support vector machine (SVM) as the classifier. The SVM is a two-class pattern classification technique that performs non-linear classification by employing a kernel function. However, the estimating unit 48 implements three-class classification by using an extension method using a plurality of classifiers such as a one-against-one technique and a one-against-all technique for the purpose of multi-class classification.

Figures 6, 7:
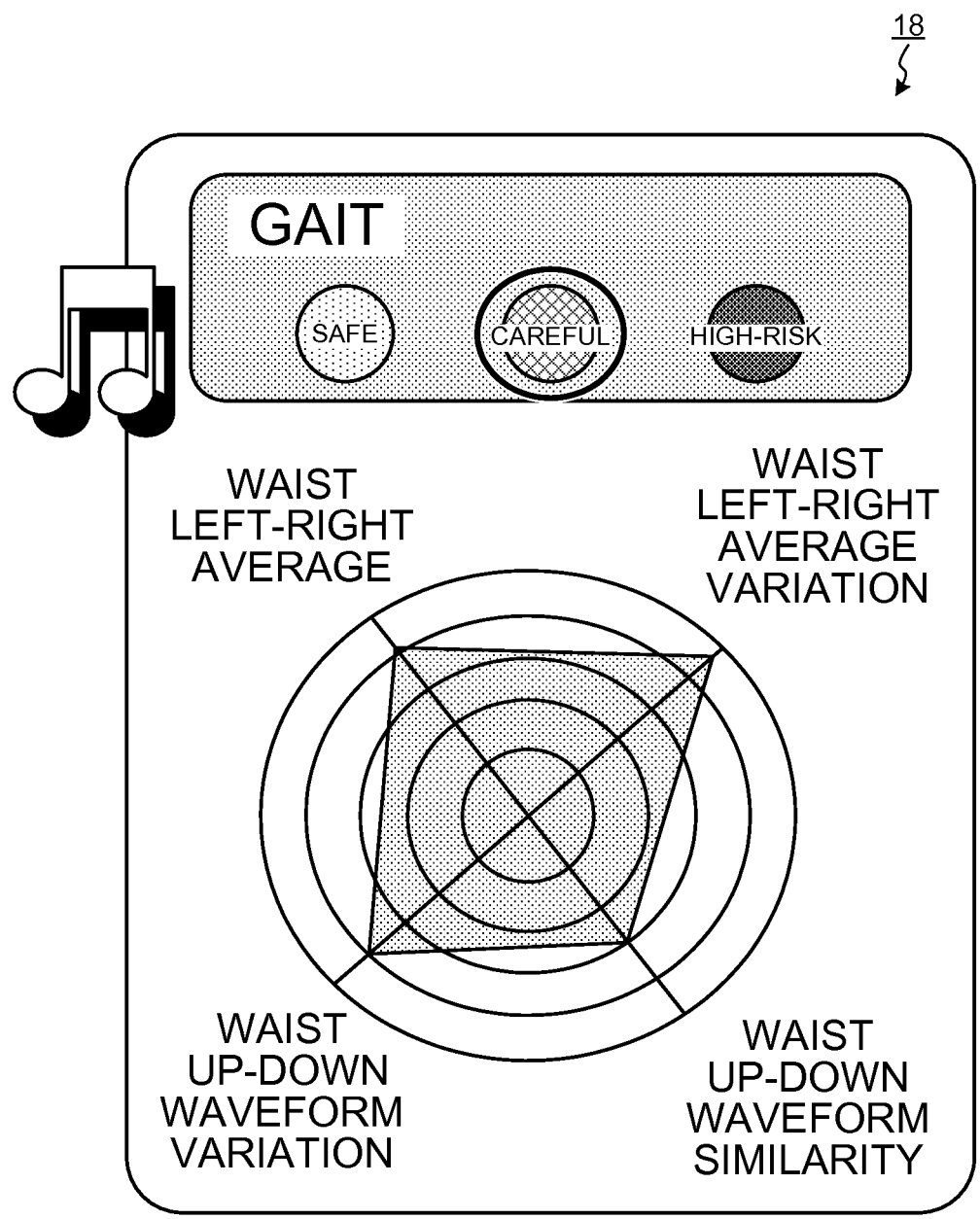
FIG. 6 is a table illustrating labels of three classes learned as a classification example.
FIG. 7 is a conceptual diagram illustrating an output example of an output unit.

For example, the estimating unit 48 classifies the subject's walking conditions into three classes illustrated in FIG. 6. Labels (class labels) of "safe", "careful", and "high-risk" are attached to the three classes, respectively.

Here, the label will be described in detail. As illustrated in FIG. 6, for example, each label is associated with a score range representing balance ability. The score range associated with each label corresponds to a berg balance scale (BBS) score. The BBS refers to a balance test including 14 kinds of actions such as standing on one foot and turning, and assesses a balance ability of an evaluation subject with a score of 0 to 56 points (each of 14 kinds of actions is scored from 0 to 4).

The estimating unit 48 is trained based on previously measured data prospectively. In advance, a feature quantity and a variation of acceleration data during gait of subjects including persons with relatively high risk of fall and persons with high balance ability are prepared as training data. The scores using the BBS for the same subjects are measured in advance. The estimating unit 48 is trained to associate the feature quantity and the variation value with a score range representing a walking condition.

In other words, the estimating unit 48 performs learning a relation between the three labels to classify a walking condition and the feature quantity and the variation value in advance, and classifies (estimates) the subject's walking condition based on the feature quantity and the variation value of the subject whose walking condition is newly analyzed.

The estimating unit 48 may be configured to estimate the subject's walking condion using at least one of the feature quantity and the variation value. The estimating unit 48 may be configured to estimate the walking condition by simply setting a threshold value to the feature quantity and the variation value without using a learning algorithm. The estimating unit 48 may use a neural network as another algorithm or may be configured to perform dimensional compression using a self-organizing map, kernel principal component analysis (kernel PCA), or the like and then execute a pattern recognition algorithm.

The output unit 18 (FIG. 3) receives and outputs the estimation result of the estimating unit 48. FIG. 7 is a conceptual diagram illustrating an output example of the output unit 18. As illustrated in FIG. 7, the output unit 18 outputs the label representing the estimation result of the estimating unit 48 through a signal such as an image on a display or a sound. The output unit 18 may be configured to output at least one of the calculation result of the analyzing unit 46 and the estimation result of the estimating unit 48.

Next, an operation of the gait analysis device 1 will be described. FIG. 8 is a flowchart of an operation when the gait analysis device 1 according to an embodiment executes a program corresponding to the function illustrated in FIG. 3. For example, the gait analysis device 1 is powered on in a state (for example, a rest state) in which a subject does not make a dynamic behavior such as walking and then starts gait analysis.

Referring to FIG. 8, in step S100, for example, when the gait analysis device 1 is powered on, the detecting unit 20 starts to detect the subject's acceleration.

In step S102, the determining unit 42 determines whether or not the first time interval "a" (that is interval "a" in FIG. 4) has elapsed. Here, when the determining unit 42 determines that the first time interval "a" has elapsed (Yes in step S102), the process proceeds to step S104. However, when it is determined that the first time interval "a" has not elapsed (No in step S102), the process of step S102 is continuously performed.

In step S104, the determining unit 42 calculates a variance of acceleration data measured by the measuring unit 40, for example, within the first setting time period A.

In step S106, the determining unit 42 determines whether or not the variance of the acceleration data calculated in the process of step S104 is equal to or less than a predetermined threshold value (threshold value σ). Here, when the determining unit 42 determines that the variance of the acceleration data is equal to or less than the threshold value σ (Yes in step S106), the process to proceed to step S108. However, when it is determined that the variance of the acceleration data is larger than the threshold value σ (No in step S106), the process proceeds to step S112. Alternatively, the process may proceed to step S102 and then continued.

In step S108, the determining unit 42 determines whether or not a time period in which the variance of the acceleration data is equal to or less than the threshold value σ lasts for a second setting time period B or more. Here, when the determining unit 42 determines that the time period in which the variance of the acceleration data is equal to or less than the threshold value σ lasts for the second setting time period B or more (Yes in step S108), the process proceeds to step S110. However, when it is determined that the time period in which the variance of the acceleration data is equal to or less than the threshold value σ does not last for the second setting time period B or more (No in step S108), the process proceeds to step S102.

In step S110, the determining unit 42 determines whether or not the variance of the acceleration data is larger than the threshold value σ. Here, when the determining unit 42 determines that the variance of the acceleration data is larger than the threshold value σ (Yes in step S110), the process proceeds to step S112. However, when it is determined that the variance of the acceleration data is equal to or less than the threshold value σ (No in step S110), the process proceeds to step S102.

In step S112, the determining unit 42 determines whether or not a time period in which the variance of the acceleration data is larger than threshold value σ lasts for a third setting time period C or more. Here, when the determining unit 42 determines that the time period in which the variance of the acceleration data is larger than threshold value σ lasts for the third setting time period C or more (Yes in step S112), the process proceeds to step S114. However, when the determining unit 42 determines that the time period in which the variance of the acceleration data is larger than threshold value σ does not last for the third setting time period C or more (No in step S112), the process proceeds to step S102.

In step S114, the determining unit 42 determines a walking start point in time.

In step S116, the extracting unit 44 receives the determination result of the determining unit 42 and extracts an analysis target.

In step S118, the feature quantity calculating unit 460 receives the data set for analysis extracted by the extracting unit 44 and calculates a feature quantity.

In step S120, the variation value calculating unit 462 receives the feature quantity calculated by the feature quantity calculating unit 460, and calculates a variation value.

In step S122, the estimating unit 48 receives at least one of the feature quantities calculated by the feature quantity calculating unit 460 and the variation value calculated by the variation value calculating unit 462, and then estimates the subject's walking condition.

In step S124, the output unit 18 outputs the estimation result calculated by the estimating unit 48.

Meanwhile, the gait analysis device 1 may be configured to estimate the subject's walking condition using all acceleration in three directions detected by the detecting unit 20 (or using an arbitrary combination of acceleration in three directions) or may be configured to estimate the subject's walking condition using at least one of the feature quantity and the variation value calculated based on acceleration data in one direction. The above-described embodiment has been described in connection with the example in which the feature quantity calculated by the feature quantity calculating unit 460 is distinguished from the variation value calculated by the variation value calculating unit 462. However, the gait analysis device 1 may be configured to estimate the subject's walking condition by regarding the variation value calculated by the variation value calculating unit 462 as one of feature quantities. In other words, the gait analysis device 1 may be configured to estimate the subject's walking condition by regarding all values calculated by the analyzing unit 46 as feature quantities corresponding to the subject's motion.

Further, in the gait analysis device 1, when the subject's walking condition is estimated based on the acceleration data of the extraction time period D1, the same time period (3 seconds in the example illustrated in FIG. 4) as the extraction time period D1 is set as an initial time period in which the subject's motion is not stabilized. Further, when the subject's walking condition is estimated based on the acceleration data of the extraction time periods D1 to D7. The extraction time period is a time period (6 seconds in the example illustrated in FIG. 4) between the walking start point in time and the end point of the extraction time period D7 and is set as a time period in which the subject's motion is not stabilized firstly.

The gait analysis device 1 is not limited to the configuration described in the above-described embodiment. For example, the gait analysis device 1 may be configured such that the main body unit 10 includes the detecting unit 20 (or the measuring unit 40) and the communication unit 22, and a personal computer (PC) or the like connected to the main body unit 10 via a network includes the determining unit 42, the extracting unit 44, the analyzing unit 46, the estimating unit 48, and the output unit 18.

The main body unit 10 may be attached directly on the subject's body with the wearing unit 30, and may be attached with an adhesive member or may be mounted to a backpack or the like.

The program executed by the gait analysis device 1 of the present embodiment is configured to include modules for implementing the above-described components (the determining unit 42, the extracting unit 44, the analyzing unit 46, and the estimating unit 48).

According to the above-described embodiment, even though a single sensor is used, since a walking condition is estimated based on a feature quantity when a subject starts walking, the subject's walking condition can be estimated in a short period of time. In addition, according to the embodiment, a fall risk can be estimated even though the subject does not do a complicated action with a high risk and a heavy burden.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A gait analysis device for observing a walking condition of a subject and preventing the subject from falling, the device comprising:
a hardware processor;
an acceleration sensor; and
a memory for storing processor-executable instructions that, when executed by the processor, cause the processor to control the gait analysis device to at least:
receive acceleration data from the acceleration sensor indicative of acceleration of the subject at or near a waist of the subject;
calculate a variance of the acceleration data in each first setting time period;
determine sequential variances are continuously equal to or less than a threshold value for a second setting timing period or longer, and thereafter the sequential variances continuously exceed the threshold value for a third setting time period or longer, and determine, as a walking start point, a time at which acceleration data corresponding to a last one of the variances equal to or less than the threshold value is obtained, the second setting time period and the third setting time period being both longer than the first setting time period; and
estimate a walking condition and a fall risk of the subject subsequent to the walking start point by at least:
calculating a feature quantity of the received acceleration data of the subject for a transitional time period that starts from the walking start point and calculating a variation based on the feature quantity, the calculated feature quantity including at least an average value of the acceleration data in a horizontal direction orthogonal to a moving direction of the subject for the transitional time period; and
estimating the risk that the subject will fall based on the calculated feature quantity and the calculated variation, the estimating using a pattern recognition algorithm that is based on a learned relationship between class labels indicative of different risk levels and values of the feature quantity and variation based thereon for test subjects while walking.

2. The device according to claim 1, wherein
the received acceleration data comprises acceleration data, which changes in response to a motion of the subject, in at least one direction.

3. The device according to claim 2, wherein
the processor-executable instructions further cause the processor to control the gait analysis device to calculate the feature quantity of the received acceleration data until the third setting time period elapses from the walking start point.

4. The device according to claim 3, wherein
the processor-executable instructions further cause the processor to control the gait analysis device to calculate the feature quantity of the received acceleration data during time periods obtained by sequentially delaying the third setting time period from the walking start point by a certain time interval.

5. The device according to claim 4, wherein the processor-executable instructions further cause the processor to control the gait analysis device to:
calculate, as the feature quantity, maximum autocorrelation values in an autocorrelation function of the acceleration in the vertical direction during the time periods and average values of the acceleration in the horizontal direction,
calculate at least one of a first variation value and a second variation value, the first variation value being a variation value of the maximum autocorrelation values, and the second variation value being a variation value of the average values, and
estimate the risk that the subject will fall based on at least one of the first variation value and the second variation value, and the feature quantity.

6. The device according to claim 5, wherein the processor-executable instructions further cause the processor to control the gait analysis device to output at least one of the first variation value, the second variation value, the feature quantity, and an estimate of the risk that the subject will fall.

7. A computer program product comprising a non-transitory computer readable medium including program instructions embodied therein, wherein the instructions, when executed by a computer of a gait analysis device, cause the computer to control the gait analysis device to execute at least:
receiving acceleration data based on sensing at or near a waist of a subject;
calculating a variance of the acceleration data in each first setting time period;
determining sequential variances are continuously equal to or less than a threshold value for a second setting timing period or longer, and thereafter the sequential variances continuously exceed the threshold value for a third setting time period or longer, and determining, as a walking start point, a time at which acceleration data corresponding to a last one of the variances equal to or less than the threshold value is obtained, the second setting time period and the third setting time period being both longer than the first setting time period; and
estimating a walking condition and a fall risk of the subject subsequent to the walking start point by at least:
calculating a feature quantity of the received acceleration data of the subject for a transitional time period that starts from the walking start point and calculating a variation based on the feature quantity, the calculated feature quantity including at least an average value of the acceleration data in a horizontal direction orthogonal to a moving direction of the subject for the transitional time period; and
estimating the risk that the subject will fall based on the calculated feature quantity and the calculated variation, the estimating using a pattern recognition algorithm that is based on a learned relationship between class labels indicative of different risk levels and values of the feature quantity and variation thereof for test subjects while walking.

* * * * *